United States Patent
Hanson et al.

(10) Patent No.: US 11,867,342 B2
(45) Date of Patent: Jan. 9, 2024

(54) FLUIDIC CHANNELS AND METHODS OF ALTERING THE SURFACE ENERGY OF COMPONENTS THEREOF

(71) Applicant: ACULON, INC., San Diego, CA (US)

(72) Inventors: Eric Lee Hanson, Carlsbad, CA (US); Eric L. Bruner, La Jolla, CA (US); Justin Hardin, Poway, CA (US); Edward W. Hughes, San Diego, CA (US)

(73) Assignee: ACULON INC., San Diego, CA (US)

( * ) Notice: Subject to any disclaimer, the term of this patent is extended or adjusted under 35 U.S.C. 154(b) by 119 days.

(21) Appl. No.: 17/465,277

(22) Filed: Sep. 2, 2021

(65) Prior Publication Data
US 2021/0404594 A1    Dec. 30, 2021

Related U.S. Application Data

(60) Continuation-in-part of application No. 16/698,503, filed on Nov. 27, 2019, which is a division of
(Continued)

(51) Int. Cl.
*F16L 58/08* (2006.01)
*B05D 1/18* (2006.01)
(Continued)

(52) U.S. Cl.
CPC .............. *F16L 58/08* (2013.01); *B05D 1/185* (2013.01); *B05D 5/08* (2013.01); *B05D 7/22* (2013.01);
(Continued)

(58) Field of Classification Search
CPC ........... F16L 58/08; B82Y 20/00; B82Y 40/00
See application file for complete search history.

(56) References Cited

U.S. PATENT DOCUMENTS

| 4,474,538 A | 10/1984 | Schmid-Schonbein et al. |
| 5,119,116 A | 6/1992 | Yu |
| (Continued) | | |

FOREIGN PATENT DOCUMENTS

KR    2006088699 A    8/2006

OTHER PUBLICATIONS

International Search Report for PCT/US2021/048869 (Year: 2021).*

*Primary Examiner* — Michael C Miggins
(74) *Attorney, Agent, or Firm* — Blynn L. Shideler; Krisanne Shideler; BLK Law Group

(57) ABSTRACT

A surface-treated fluidic channel is provided comprising a dispensing device that comprises a microarray of microchannels. The fluidic channel is made from metal and comprises a surface and a hydrophobic coating layer comprising a self-assembled monolayer of an organophosphorus acid adhered to the surface. A mesh nebulizer comprising a reservoir and a dispensing device comprising a microarray of microchannels is also provided. A metal surface layer is applied to the interior and exterior surfaces of the reservoir and dispensing device, and a hydrophobic coating layer comprising an organo-silicon or a self-assembled monolayer of an organophosphorus acid is adhered to the metal surface layer, usually on the exterior surfaces of the reservoir and dispensing device. A hydrophilic polymeric coating layer may be chemically bonded to and propagated from terminal functional groups on the hydrophobic coating layer on the interior surfaces of the reservoir and dispensing device.

8 Claims, 3 Drawing Sheets

Related U.S. Application Data application No. 13/507,981, filed on Aug. 10, 2012, now abandoned.

(60) Provisional application No. 63/073,699, filed on Sep. 2, 2020, provisional application No. 61/574,935, filed on Aug. 11, 2011.

(51) Int. Cl.
*B82Y 40/00* (2011.01)
*B82Y 30/00* (2011.01)
*B05D 7/22* (2006.01)
*B05D 5/08* (2006.01)

(52) U.S. Cl.
CPC ............... *B82Y 30/00* (2013.01); *B82Y 40/00* (2013.01); *B05D 2202/00* (2013.01); *B05D 2350/65* (2013.01)

(56) References Cited

U.S. PATENT DOCUMENTS

| | | |
|---|---|---|
| 6,470,144 B1 | 10/2002 | Tarutani et al. |
| 6,587,343 B2 | 7/2003 | Novotny et al. |
| 7,156,117 B2 | 1/2007 | Bohm |
| 7,367,970 B2 | 5/2008 | Govari et al. |
| 7,517,546 B2 | 4/2009 | Hofer |
| 7,837,299 B2 | 11/2010 | Mori |
| 8,127,772 B2 * | 3/2012 | Montaser ............. A61M 11/042 128/200.14 |
| 2003/0105513 A1 | 6/2003 | Moriuchi et al. |
| 2003/0186914 A1 * | 10/2003 | Hofer .................... B82Y 15/00 850/52 |
| 2004/0236415 A1 | 11/2004 | Thomas |
| 2007/0092640 A1 | 4/2007 | Bruner et al. |
| 2008/0152930 A1 | 6/2008 | Hanson et al. |
| 2013/0037161 A1 | 2/2013 | Hanson et al. |
| 2020/0016617 A1 | 5/2020 | Hanson et al. |
| 2021/0120878 A1 * | 4/2021 | Bayat ................. B05B 17/0676 |

\* cited by examiner

FLUIDIC CHANNELS AND METHODS OF ALTERING THE SURFACE ENERGY OF COMPONENTS THEREOF

CROSS REFERENCE TO RELATED APPLICATIONS

The present application is continuation-in-part of U.S. patent application Ser. No. 16/698,503, filed Nov. 27, 2019, titled "TREATING FLUIDIC CHANNELS", which is a divisional of U.S. patent application Ser. No. 13/507,981, filed Aug. 10, 2012, titled "TREATING FLUIDIC CHANNELS", abandoned, which in turn claims priority to U.S. Provisional Patent Application Ser. No. 61/574,935, filed Aug. 11, 2011. The present application also claims priority to U.S. Provisional Patent Application Ser. No. 63/073,699, filed Sep. 2, 2020. All of the above applications are incorporated by reference herein in their entireties.

FIELD OF THE INVENTION

The present invention relates to the treatment of fluidic channels such as those in a closed system where a fluid such as a liquid or a gas is circulated for cooling purposes, or an open system where the channel is connected at one end to a material source and at the other end to an opening such as a nozzle for distributing the material. More particularly, this invention relates to fluidic channels, mesh nebulizers and methods of altering the surface energy of components thereof.

BACKGROUND OF THE INVENTION

Controlling the movement of fluids through channels is important in a number of technologies. Often surface effects of the channel adversely affect the fluid flow. Metals such as steel and aluminum are common industrial fluidic channel materials and can have unbound electrons; exposed polar molecules that can generate a surface charge and become reactive with the fluid. This reactivity can impede flow and even form a deposit within the channel further impeding flow. The use of surface treatments to change surface energy and thus the wetting properties of fluids on surfaces is widely known. However, the existing surface treatments generally have difficulty retaining a consistent surface energy over time. For example, some hydrophobic (low surface energy) coatings may hydrolyze and increase in surface energy, while hydrophilic coatings (high surface energy) tend to lose their hydrophilic components because the hydrophilic components dissolve in water, causing the surface energy to decrease over time. Coating the interior walls of elements with a channel with a coating that would repel the fluids may not be satisfactory, particularly with microchannels, because the thickness of the conventional coatings may itself impede flow.

A nebulizer (or nebuliser) is a device for producing a fine spray or mist of liquid. In medicine, a nebulizer is a drug delivery device used to administer medication in the form of an atomized mist inhaled into the lungs. Nebulizers are commonly used for the treatment of asthma, cystic fibrosis, COPD and other respiratory diseases or disorders. Recent improvements in nebulizer technologies have led to the development of "mesh nebulizers" using micropumps for aerosol production. The micropumps force liquid medications through multiple microscopic apertures (microfluidic channels) in a mesh or aperture plate in order to generate aerosol.

Mesh nebulizers can be classified into two categories: (1) active mesh nebulizers and (2) passive mesh nebulizers. Active mesh nebulizers use a piezo element that contracts and expands on application of an electric current and vibrates a precisely drilled mesh in contact with the medication in order to generate aerosol. Passive mesh nebulizers use a transducer horn that induces passive vibrations in the perforated plate with hundreds or even thousands of tapered microfluidic channels to produce aerosol.

On the microscopic scales (e. g., micron to nanometer level) common in the microfluidic channels present in mesh nebulizers, surface tensions of fluids and substrates (reservoirs, channels, pores, etc.) must be balanced in order to maintain consistent fluid flow. Not only is it important to control this balance initially, but to retain this balance throughout the service life of the apparatus even when in contact with materials such as surfactants, drug compounds, lipids, proteinaceous compounds, enzymes, DNA/RNA, etc., which may change the surface energy of the apparatus surfaces because of adsorption onto the apparatus surfaces.

It would be desirable to provide a fluidic channel demonstrating combinations of surface treatments capable of imparting a wide variance of surface energy to the component surfaces, as well as retaining that surface energy when the device is exposed to various fluids. It would also be desirable to provide methods of altering the surface energy of components of a fluidic channel, particularly a microchannel, such as a mesh nebulizer.

SUMMARY OF THE INVENTION

The present invention provides a surface-treated fluidic channel comprising a dispensing device that comprises a microarray of microchannels. The fluidic channel is made from metal and comprises:
1) a surface; and
2) a hydrophobic coating layer comprising a self-assembled monolayer of an organophosphorus acid adhered to the surface, wherein the hydrophobic coating layer is adhered to the surface either directly or indirectly through an intermediate organometallic coating.

The present invention further provides a mesh nebulizer comprising a reservoir and a dispensing device that comprises a microarray of microchannels, wherein the reservoir and dispensing device are configured to allow a fluid to flow from the reservoir through the dispensing device and exit the dispensing device as an aerosol. The reservoir and dispensing device comprise:
1) an interior surface;
2) an exterior surface that opposes the interior surface;
3) a metal surface layer applied to the interior and exterior surfaces and comprising one or more of silver, gold, palladium, platinum, rhodium, iridium, tantalum, aluminum, copper, titanium, iron, chromium, alloys thereof, and oxides thereof; and
4) a hydrophobic coating layer comprising an organosilicon or a self-assembled monolayer of an organophosphorus acid, adhered to the metal surface layer on the interior and/or exterior surface of the reservoir and dispensing device, wherein the hydrophobic coating layer is adhered to the metal surface layer either directly or indirectly through an intermediate organometallic coating.

A method of altering the surface energy of one or more components of a mesh nebulizer is additionally provided. The method comprises: a) depositing a metal surface layer on surfaces of the components, wherein the metal surface layer comprises one or more of silver, gold, palladium, platinum, rhodium, iridium, tantalum, aluminum, copper, titanium, iron, chromium, alloys thereof, and oxides thereof; b) forming a hydrophobic coating layer comprising an organo-silicon or a self-assembled monolayer of an organo-phosphorus acid directly on the metal surface layer or indirectly on the metal surface layer through an intermediate organometallic coating; and c) removing select areas of the hydrophobic coating layer to expose the metal surface layer.

The mesh nebulizers of the present invention are resistant to environmental attack such as by hydrolysis, thermolysis, enzymatic breakdown, etc., and contaminant adsorption (e. g., surfactants, drug compounds, lipids, proteinaceous compounds, enzymes, DNA/RNA, etc.)

Figure 1:
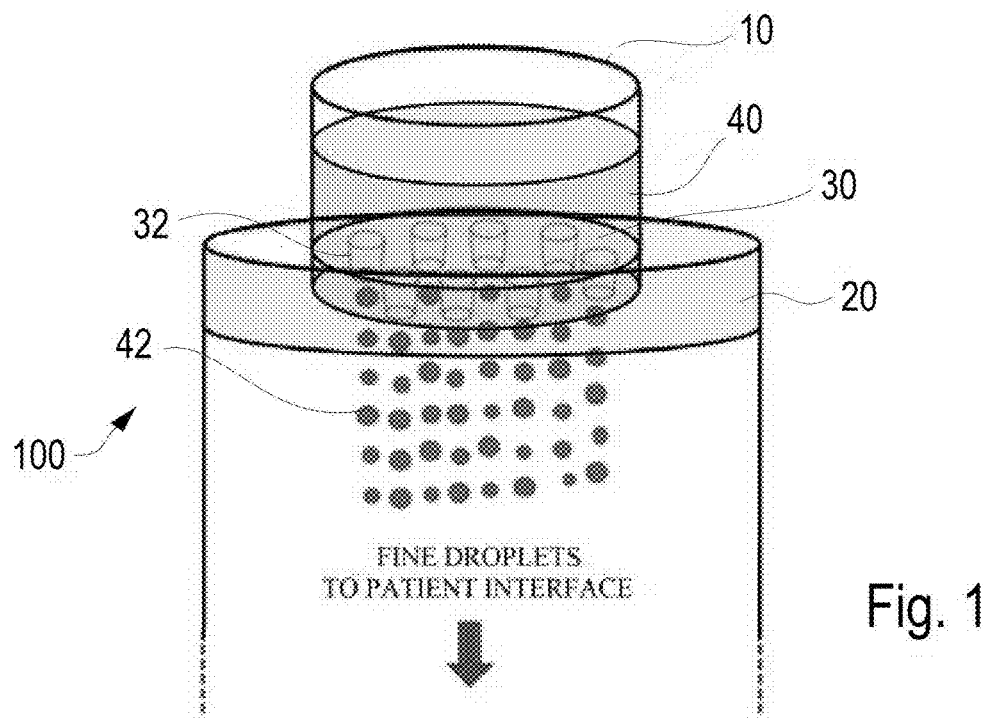
FIG. 1 is a schematic representation of a piezo-type mesh nebulizer filled with a fluid and having reservoir and dispensing device components in accordance with the present invention.

FIG. 2A is a schematic cross-sectional representation of portion of a device associated with a fluidic channel of the present invention, including interior and exterior metal surface and hydrophobic coating layers with an optional intermediate organometallic coating.

FIG. 2B is a schematic cross-sectional representation of a device associated with a fluidic channel of the present invention, including interior and exterior metal surface and hydrophobic coating layers without an optional intermediate organometallic coating, and illustrating a microchannel that is also coated with these layers.

FIG. 3A is a schematic cross-sectional representation of a device associated with a fluidic channel of the present invention, including interior and exterior metal surface and hydrophobic coating layers without an optional intermediate organometallic coating, and illustrating select areas of the hydrophobic coating layer removed to expose the metal surface layer.

FIG. 3B is a schematic cross-sectional representation of a dispensing device associated with a fluidic channel of the present invention and illustrating a microchannel, including a metal surface layer on the interior and exterior of the dispensing device as well as on the surface of the micro-channel and a hydrophobic coating layer on the exterior of the dispensing device as well as on the metal surface layer in the microchannel.

FIG. 4A is a schematic cross-sectional representation of a component of a fluidic channel of the present invention, including interior and exterior metal surface, intermediate organometallic, and hydrophobic coating layers, and a polymeric coating layer chemically bonded to the hydrophobic coating layer on the interior surface of the component.

FIG. 4B is a schematic cross-sectional representation of a component of a fluidic channel of the present invention, including interior and exterior metal surface and hydrophobic coating layers (no intermediate organometallic coating), with a polymeric coating layer chemically bonded to the hydrophobic coating layer on the interior surface of the component.

FIG. 4C is a schematic cross-sectional representation of a dispensing device associated with a fluidic channel of the present invention, including interior and exterior metal surface and hydrophobic coating layers without an optional intermediate organometallic coating, and illustrating a microchannel that is also coated with these layers. There is additionally a hydrophilic polymeric coating layer chemically bonded to the hydrophobic coating layer on the interior surface of the dispensing device.

FIG. 4D is a schematic cross-sectional representation of a dispensing device associated with a fluidic channel of the present invention, including interior and exterior metal surface and hydrophobic coating layers without an optional intermediate organometallic coating, and illustrating a microchannel that is also coated with these layers. There is additionally a hydrophilic polymeric coating layer chemically bonded to the hydrophobic coating layer on the interior surface of the dispensing device and inside the microchannel.

DETAILED DESCRIPTION OF THE INVENTION

Other than in any operating examples, or where otherwise indicated, all numbers expressing quantities of ingredients, reaction conditions and so forth used in the specification and claims are to be understood as being modified in all instances by the term “about.” Accordingly, unless indicated to the contrary, the numerical parameters set forth in the following specification and attached claims are approximations that may vary depending upon the desired properties to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

Also, it should be understood that any numerical range recited herein is intended to include all sub-ranges subsumed therein. For example, a range of “1 to 10” is intended to include all sub-ranges between (and including) the recited minimum value of 1 and the recited maximum value of 10, that is, having a minimum value equal to or greater than 1 and a maximum value of equal to or less than 10.

As used in this specification and the appended claims, the articles “a,” “an,” and “the” include plural referents unless expressly and unequivocally limited to one referent.

The various aspects and examples of the present invention as presented herein are each understood to be non-limiting with respect to the scope of the invention.

The present invention provides fluidic channels such as mesh nebulizers 100 as shown in FIG. 1, comprising a reservoir 10 for holding a fluid 40 to be atomized, and a dispensing device 30 comprising an activating element 20 such as a piezo element and a microarray of microchannels 32, such as a mesh, atomizer, membrane, or perforated plate, through which the fluid 40 is atomized to form aerosol droplets 42. The microchannels 32 are micro-dimensional fluidic channels (e. g., having average diameters on a micron or nanometer scale). In microtechnology, a microchannel is understood to have a hydraulic diameter below 1 millimeter. The term “fluidic channel” or “fluid channel” means a conduit of circular, oval or rectangular configuration through which a fluid such as a liquid or gas is passed. The reservoir 10 and dispensing device 30 are configured to allow fluid flow from the reservoir 10 through the dispensing device 30. The reservoir 10 and dispensing device 30 may be made of any metal or polymeric material that allows for the deposition of a metal surface layer onto surfaces of the material. Typical metals include nickel, palladium, and alloys thereof.

The reservoir 10 and dispensing device 30 each comprise 1) an interior surface that is oriented toward the source of the fluid 40, and 2) an exterior surface that opposes the interior surface. Because the interior surface 1) is oriented toward the source of the fluid 40, which is typically an aqueous solution or dispersion, it is coated as described below in order to be rendered hydrophilic, which allows for consistent wetting by the fluid 40. Typical fluids comprise aqueous solutions of medications to be delivered to a patient in the form of a mist usually inhaled into the lungs, such as nicotine solutions, drugs for the treatment of COPD, asthma medications such as albuterol or corticosteroids, etc. The term "solutions" is meant to include homogeneous mixtures of one substance in another. Liquid solutions are optically clear because the particle size of the dissolved material is less than the wavelength of visible light. The term solution also includes "dispersions" that are non-homogeneous mixtures of one substance in another. Liquid dispersions are translucent and also include emulsions that are optically opaque because the particle size of the dispersed particle is greater than the wavelength of visible light. The dispersed material itself may be of such particle size or it may associate with itself or the dispersing medium forming micelles.

Consistent wetting facilitates droplet formation through a maximum number of the microchannels 32. The exterior surface 2) is coated as described below in order to be rendered hydrophobic to allow for consistent droplet size formation across the area of the dispensing device 30. Moreover, droplet size remains uniform over time; i. e., the life of the mesh nebulizer. By "hydrophilic" is meant that a material has polar properties and has a tendency to interact with or be attracted to ("wetted" by) water and other polar substances. By "hydrophobic" is meant that a material has non-polar properties and has a tendency to cause water to bead due to surface tension differences between water and the material.

The reservoir 10 and dispensing device 30 further comprise 3) a metal surface layer 52 and 4) a hydrophobic coating layer 56 adhered to the metal surface layer 52. The metal surface layer 52 is deposited on interior and exterior surfaces of the reservoir 10 and dispensing device 30. The metal surface layer 52 that is deposited may comprise one or more of aluminum, iron, chromium, titanium, tantalum, and noble metals such as rhodium, palladium, silver, iridium, platinum, gold, and copper. Alloys and oxides of these metals are also suitable, such as stainless steel. The invention is particularly useful with metal surface layers 52 that contain surface hydroxyl or oxide groups, such as native oxide layers that may spontaneously form and are associated with many metals and their alloys. These groups are believed to aid in the development of a self-assembled monolayer such as that described below.

Deposition of the metal surface layer 52 may be accomplished by chemical vapor deposition or physical vapor deposition such as thermal evaporation or sputtering, electron beam evaporation, or electroless metal deposition from solution. The thickness of the metal surface layer 52 typically ranges from 10 nm to 500 nm, such as 25 nm to 100 nm.

Figure 2A:
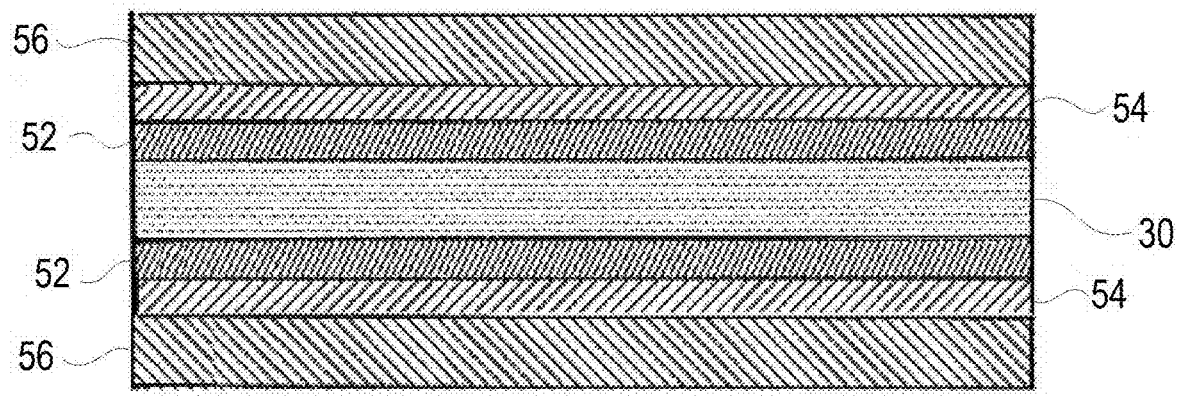
Figure 2B:
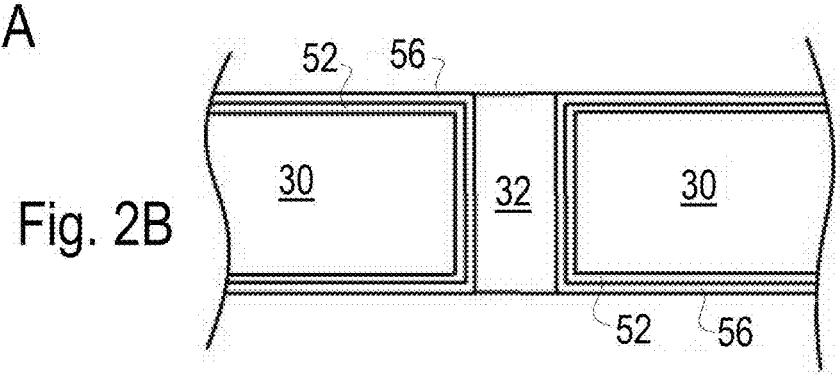
Figure 3A:
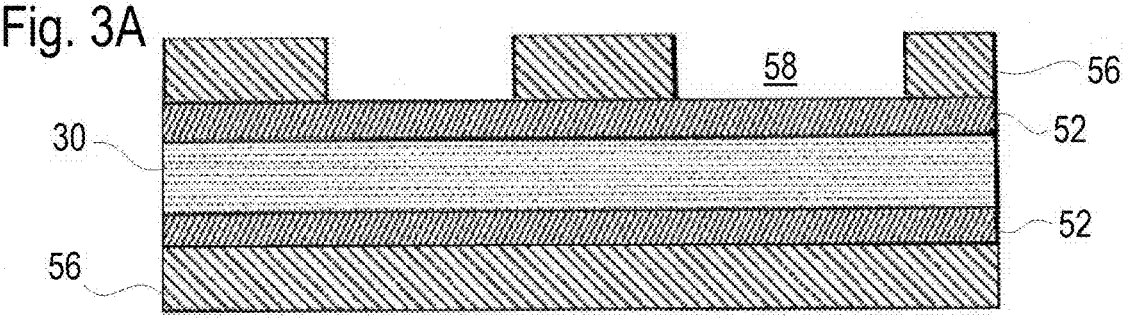
Figure 3B:
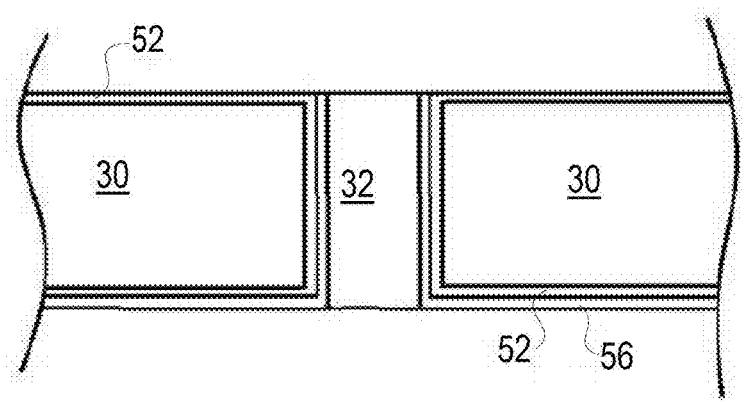
Figure 4A:
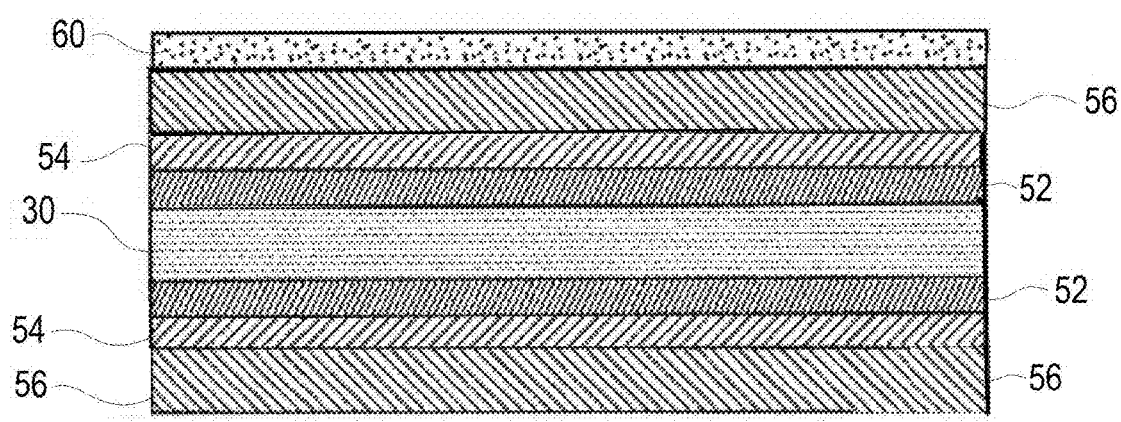
Figure 4B:
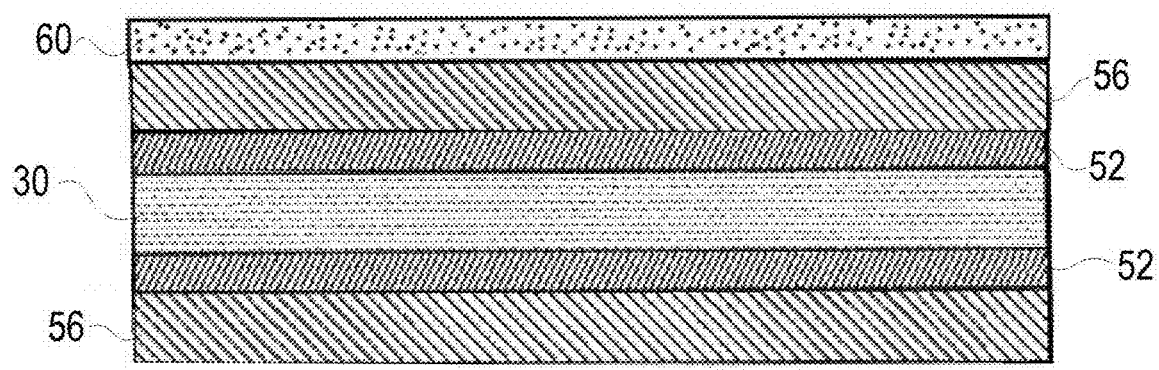

A hydrophobic coating layer 56 comprising an organo-silicon or self-assembled monolayer of an organophosphorus acid is adhered to the metal surface layer 52. Adherence may be through physical attraction or through chemically bonding, and the hydrophobic coating layer 56 is adhered to the metal surface layer 52 either directly, as shown in FIGS. 2B, 3A, 3B, 4B, 4C, and 4D, or indirectly through an intermediate organometallic coating 54, as shown in FIGS. 2A and 4A.

Suitable organo-silicon compounds used to form the hydrophobic coating layer 56 include organosiloxanes, trihalosilanes, tetrahalosilanes such as perfluorosilane, organosilanes such as alkoxysilanes, and polymers (including sol-gels) thereof. Mixtures of compounds may also be used. Often the hydrophobic coating layer 56 is essentially free of metal oxides.

Suitable trihalosilanes include alkyltrihalosilanes, such as alkyltrifluorosilanes, alkyltrichlorosilanes, and alkyltribromosilanes. Examples of suitable alkyltrichlorosilanes include methyltrichlorosilane, vinyltrichlorosilane, ethyltrichlorosilane, n-propyltrichlorosilane, i-propyltrichlorosilane, γ-chloropropyltrichlorosilane, i-butyltrichlorosilane, n-butyltrichlorosilane, pentyltrichlorosilane, hexyltrichlorosilane, heptyltrichlorosilane, n-octyltrichlorosilane, i-octyltrichlorosilane, hexadecyltrichlorosilane, 10-undecenyltrichlorosilane, 13-tetradecenyltrichlorosilane, 14-pentadecenyltrichlorosilane, 15-hexadecenyltrichlorosilane, n-octadecyltrichlorosilane and n-hexadecyltrichlorosilane.

Suitable organosilanes typically have the structure:

$$SiR_4$$

wherein each R independently comprises H or an organic group selected from linear, branched, or cyclic alkyl having 1 to 12 carbon atoms; alkoxy; and polyalkoxy; and wherein at least one R comprises an organic group. Alkyl groups may be substituted with functional groups such as halo-, aldehyde, epoxy, hydroxyl, and the like, for particular applications. Examples of suitable organosilanes include trimethoxysilane and glycidylpropyl trimethoxysilane. An example of a polymeric organosilane is trimethoxysilyl-terminated polyperfluorosilane. In a particular example of the present invention, an alkoxysilane is applied as the hydrophobic coating layer 56 over a metal surface layer 52 comprising tantalum or oxides thereof. In this example of the present invention, the hydrophobic coating layer 56 may be adhered directly to the metal surface layer 52 without an intermediate organometallic coating 54.

The organo-silicon compound may be dissolved in a solvent such as an aprotic solvent. An exemplary solvent is 3-ethoxyperfluoro(2-methylhexane) (HFE 7500, available from 3M). The hydrophobic coating layer 56 comprising an organo-silicon compound may be applied to the metal surface layer 52 by one or more of a number of methods such as spraying, dipping (immersion), spin coating, or flow coating onto a surface thereof. The hydrophobic coating layer 56 comprising an organo-silicon compound may also be applied as a sol-gel layer, deposited onto the metal surface layer 52 from, for example, a solution of hydrolyzed trialkoxysilane in an alcohol having 1 to 6 carbon atoms, such as isopropanol.

When an organo-silicon is used in the hydrophobic coating layer 56, the coated component may be subjected to elevated temperatures, such as at least 80° C., or at least 120° C., for a time sufficient to at least partially cure the hydrophobic coating layer 56. Durations of at least 30 minutes, depending on the temperature, such as at least 2 hours, are typical.

The term "cure", "cured" or similar terms, as used in connection with a cured or curable composition, e.g., a "cured composition" of some specific description, means that at least a portion of any polymerizable and/or crosslinkable components that form the curable composition is polymerized and/or crosslinked. Additionally, curing of a composition refers to subjecting said composition to curing conditions such as those listed above, leading to the reaction of the reactive functional groups of the composition. The term "at least partially cured" means subjecting the composition to curing conditions, wherein reaction of at least a portion of the reactive groups of the composition occurs. The composition can also be subjected to curing conditions such that a substantially complete cure is attained and wherein further curing results in no significant further improvement in physical properties, such as hardness.

When an organo-silicon is used in the hydrophobic coating layer 56, the hydrophobic coating layer 56 typically has a final dry film thickness (DFT) of 4-10 nm.

The hydrophobic coating layer 56 may alternatively comprise a self-assembled monolayer of an organophosphorus acid. The organophosphorus acid may be an organophosphoric acid, an organophosphonic acid or an organophosphinic acid. The organo groups may be monomeric or polymeric.

Examples of monomeric phosphoric acids are compounds or mixtures of compounds having the following structure:

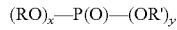

(RO)$_x$—P(O)—(OR')$_y$ wherein x is 1-2, y is 1-2 and x+y=3; R is a radical having a total of 1-30, often 6-18 carbons; R' is H, a metal such as an alkali metal, for example, sodium or potassium or lower alkyl having 1 to 4 carbons, such as methyl or ethyl. Usually, a portion of R' groups comprise H. The organic component of the phosphoric acid (R) can be aliphatic (e.g., alkyl having 2-20, often 6-18 carbon atoms) including an unsaturated carbon chain (e.g., an olefin), or can be aryl or aryl-substituted moiety. At least one of the organo groups can contain terminal or omega functional groups as described below.

Examples of monomeric phosphonic acids are compounds or mixtures of compounds having the formula:

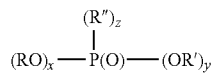

(R")$_z$
|
(RO)$_x$—P(O)—(OR')$_y$ wherein x is 0 or 1, y is 1 or 2, z is 1 and x+y+z is 3. R and R" are each independently a radical having a total of 1-30, usually 6-18 carbons. R' is H, a metal, such as an alkali metal, for example, sodium or potassium or lower alkyl having 1-4 carbons such as methyl or ethyl.

Usually, at least a portion of R' groups comprise H. The organic component of the phosphonic acid (R and R") can be aliphatic (e.g., alkyl having 2-20, usually 6-18 carbon atoms) including an unsaturated carbon chain (e.g., an olefin), or can be an aryl or aryl-substituted moiety. At least one of the organo groups can contain terminal or omega functional groups as described below.

Examples of monomeric phosphinic acids are compounds or mixtures of compounds having the formula:

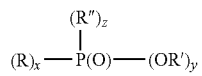

(R")$_z$
|
(R)$_x$—P(O)—(OR')$_y$ wherein x is 0-2, y is 0-2, z is 0-2 and x+y+z is 3. R and R" are each independently radicals having a total of 1-30, usually 6-18 carbons. R' is H, a metal, such as an alkali metal, for example, sodium or potassium or lower alkyl having 1-4 carbons, such as methyl or ethyl.

Usually, at least a portion of R' groups comprise H. The organic component of the phosphinic acid (R, R") can be aliphatic (e.g., alkyl having 2-20, usually 6-18 carbon atoms) including an unsaturated carbon chain (e.g., an olefin), or can be an aryl or aryl-substituted moiety.

Examples of organo groups which may comprise R and R" include long and short chain aliphatic hydrocarbons, aromatic hydrocarbons and substituted aliphatic hydrocarbons and substituted aromatic hydrocarbons. Examples of substituents include fluoro and perfluoro such as $CF_3(C_nF_{2n})$ $CH_2CH_2PO_3H_2$. At least one of the organo groups can contain terminal or omega functional groups as described below. Examples of terminal or omega functional groups include carboxyl such as carboxylic acid, hydroxyl, amino, imino, amido, thio and phosphonic acid.

Examples of the organophosphorus acids include amino trismethylene phosphonic acid, aminobenzylphosphonic acid, 3-amino propyl phosphonic acid, O-aminophenyl phosphonic acid, 4-methoxyphenyl phosphonic acid, aminophenylphosphonic acid, aminophosphonobutyric acid, aminopropylphosphonic acid, benzohydrylphosphonic acid, benzylphosphonic acid, butylphosphonic acid, carboxyethylphosphonic acid, diphenylphosphinic acid, dodecylphosphonic acid, ethylidenediphosphonic acid, heptadecylphosphonic acid, methylbenzylphosphonic acid, naphthylmethylphosphonic acid, octadecylphosphonic acid, octylphosphonic acid, pentylphosphonic acid, phenylphosphinic acid, phenylphosphonic acid, bis-(perfluoroheptyl) phosphinic acid, perfluorohexyl phosphonic acid, styrene phosphonic acid, dodecyl bis-1,12-phosphonic acid.

In addition to the monomeric organophosphorus acids, oligomeric or polymeric organophosphorus acids resulting from self-condensation of the respective monomeric acids may be used, where R and/or R" is an alkane, olefin, perfluoroalkane, or perfluoroalkylether such as described above, or where R and/or R" is a group of the structure:

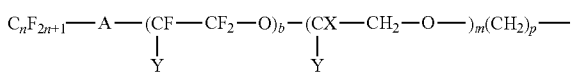

$C_nF_{2n+1}$—A—(CF—CF$_2$—O)$_b$—(CX—CH$_2$—O—)$_m$(CH$_2$)$_p$—
                  |                    |
                  Y                    Y where A is an oxygen radical or a chemical bond; n is 1 to 20; Y is H, F, $C_nH_{2n+1}$ or $C_nF_{2n+1}$; X is H or F; b is at least 1, m is 0 to 50, and p is 1 to 20.

The organophosphorus acid is typically dissolved or dispersed in a diluent to form a solution. Suitable diluents include alcohols such as methanol, ethanol or propanol; aliphatic hydrocarbons such as hexane, isooctane and decane, ethers, for example, tetrahydrofuran and dialkylethers such as diethylether. Diluents for fluorinated materials can include perfluorinated compounds such as perfluorinated tetrahydrofuran. Also, aqueous alkaline solutions such as sodium and potassium hydroxide can be used as the diluent.

Adjuvant materials may be present in the organophosphorus acid solution. Examples include surface active agents, stabilizers, and anti-static agents. The adjuvants if present are present in amounts of up to 30 percent by weight, based on the non-volatile content of the organic acid composition.

The concentration of the organophosphorus acid in the solution is not particularly critical but is at least 0.01 millimolar, typically 0.01 to 100 millimolar, and more typically 0.1 to 50 millimolar. The solution can be prepared by mixing all of the components at the same time or by adding the components in several steps.

The organophosphorus acid solution can be contacted with the metal surface layer 52 typically by immersion, spraying, flow coating, brush application or the like, followed by evaporating the solution medium at ambient temperatures or by the application of heat to effect formation of the self-assembled monolayer.

As noted above, adherence of the hydrophobic coating layer 56 to the metal surface layer 52 may be through physical attraction or through chemically bonding. With physical attraction it is believed the organophosphorus acid is in the form of the acid, rather than a salt or ester. In the case of chemical bonding, it is believed the acid forms an ionic or covalent bond with reactive groups on the metal surface layer.

The resultant self-assembled monolayer typically is of nano dimensions, having a thickness of no greater than 100 nm, typically about 10-100 nanometers. The layer is hydrophobic, having a water contact angle greater than 70°, typically from 75-130°. The water contact angle can be determined using a contact angle goniometer such as a TANTEC contact angle meter Model CAM-MICRO.

The hydrophobic coating layer 56 may be adhered to the metal surface layer 52 either directly or indirectly through an intermediate organometallic coating 54. When better adhesion and durability than that afforded by direct application is desired, an organometallic coating should be applied to the metal surface layer 52 followed by application of the organophosphorus acid. However, when the metal surface layer 52 comprises tantalum or an oxide thereof, and/or when the hydrophobic coating layer 56 comprises an organo-silicon, an intermediate organometallic coating is not necessary.

The organometallic compound used in the intermediate organometallic coating 54 is usually derived from a metal or metalloid, often a transition metal, selected from Group III and Groups IIIB, IVB, VB and VIB of the Periodic Table. Transition metals are used most often, such as those selected from Groups IIIB, IVB, VB and VIB of the Periodic Table. Examples are tantalum, titanium, zirconium, lanthanum, hafnium and tungsten. Niobium is also a suitable metal. The organo portion of the organometallic compound is selected from those groups that are reactive with the organophosphorus acid. Also, as will be described later, the organo group of the organometallic compound is believed to be reactive with groups on the surfaces being treated such as oxide and hydroxyl groups. Examples of suitable organo groups of the organometallic compound are alkoxide groups containing from 1 to 18, usually 2 to 4 carbon atoms, such as ethoxide, propoxide, isopropoxide, butoxide, isobutoxide, tert-butoxide and ethylhexyloxide. Mixed groups such as alkoxide, acetyl acetonate and chloride groups can be used.

The organometallic compounds can be in the form of simple alkoxylates or polymeric forms of the alkoxylate, and various chelates and complexes. For example, in the case of titanium and zirconium, the organometallic compound can include one or more of:

a) alkoxylates of titanium and zirconium having the general formula $M(OR)_4$, wherein M is selected from Ti and Zr and R is $C_{1-18}$ alkyl, b) polymeric alkyl titanates and zirconates obtainable by condensation of the alkoxylates of (a), i.e., partially hydrolyzed alkoxylates of the general formula $RO[-M(OR)_2O]_{x-1}R$, wherein M and R are as above and x is a positive integer, c) titanium chelates, derived from ortho titanic acid and polyfunctional alcohols containing one or more additional hydroxyl, halo, keto, carboxyl or amino groups capable of donating electrons to titanium. Examples of these chelates are those having the general formula:

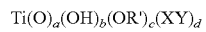

$$Ti(O)_a(OH)_b(OR')_c(XY)_d$$

wherein a=4-b-c-d; b=4-a-c-d; c=4-a-b-d; d=4-a-b-c; R' is H, $C_{1-18}$ alkyl, or X-Y, wherein X is an electron donating group such as oxygen or nitrogen and Y is an aliphatic radical having a two- or three-carbon atom chain such as I. —$CH_2CH_2$—, e.g., of ethanolamine, diethanolamine and triethanolamine;

II.

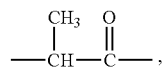

e.g., of lactic acid;

III.

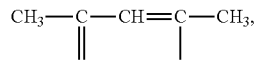

e.g., of acetylacetone enol form; or

IV.

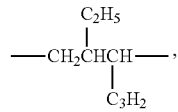

e.g., as in 1,3-octyleneglycol;

d) titanium acrylates having the general formula $Ti(OCOR)_{4-n}(OR)_n$, wherein R is $C_{1-18}$ alkyl as above and n is an integer of from 1 to 3, and polymeric forms thereof, or e) mixtures thereof.

The organometallic compound can be dissolved or dispersed in a diluent to form a solution. Examples of suitable diluents are alcohols such as methanol, ethanol and propanol, aliphatic hydrocarbons, such as hexane, isooctane and decane, ethers, for example, tetrahydrofuran and dialkyl ethers such as diethyl ether. The concentration of the organometallic compound in the solution is not particularly critical but is usually at least 0.01 millimolar, typically from 0.01 to 100 millimolar, and more typically from 0.1 to 50 millimolar.

Also, adjuvant materials may be present in the solution. Examples include stabilizers such as sterically hindered alcohols, surfactants and anti-static agents. The adjuvants if present are present in amounts of up to 30 percent by weight, based on the non-volatile content of the composition.

The organometallic treatment solution can be prepared by mixing all of the components at the same time or by combining the ingredients in several steps. If the organometallic compound chosen is reactive with moisture, (e.g. in the case of titanium (IV) n-butoxide, tantalum (V) ethoxide, aluminum (III) isopropoxide, etc.), care should be taken that moisture is not introduced with the diluent or adjuvant materials and that mixing is conducted in a substantially anhydrous atmosphere.

The organometallic solution can be contacted with the metal surface layer 52 typically by immersion, spraying, flow coating, brush application or the like, followed by removing excess solution and evaporating the diluent. This can be accomplished by heating to 50-200° C. or by simple exposure to ambient temperature, that is, from 20-25° C. Alternatively, the organometallic compound can be used neat and applied by vapor deposition techniques.

The resulting film may be in the form of a polymeric metal oxide with unreacted alkoxide and hydroxyl groups. This is accomplished by depositing the film under conditions resulting in hydrolysis and self-condensation of the alkoxide. These reactions result in a polymeric metal oxide coating being formed. The conditions necessary for these reactions to occur is to deposit the film in the presence of water, such as a moisture-containing atmosphere; however, these reactions can be performed in solution by the careful addition of water. The resulting film has some unreacted alkoxide groups and/or hydroxyl groups for subsequent reaction and possible covalent bonding with the organophosphorus acid. Note that the phrase "and/or" when used in a list is meant to encompass alternative embodiments including each individual component in the list as well as any combination of components. For example, the list "A, B, and/or C" is meant to encompass seven separate embodiments that include A, or B, or C, or A+B, or A+C, or B+C, or A+B+C.

Although not intending to be bound by any theory, it is believed the polymeric metal oxide is of the structure:

$$[M(O)_x(OH)_y(OR)_z]_n$$

where M is the metal being used, R is an alkyl group containing from 1 to 30 carbon atoms; $x+y+z=V$, the valence of M; x is at least 1, y is at least 1, z is at least 1; $x=V-y-z$; $y=V-x-z$; $z=V-x-y$; n is greater than 2, such as 2 to 1000.

When the organometallic compound is used neat and applied by chemical vapor deposition techniques in the absence of moisture, a thin metal alkoxide film is believed to form. Polymerization, if any occurs, is minimized and the film may be in monolayer configuration. The resulting film 54 typically has a thickness of 0.5 to 100 nanometers. When the organometallic compound is subjected to hydrolysis and self-condensation conditions as mentioned above, somewhat thicker films are formed.

Although not intending to be bound by any theory, it is believed the acid groups of the organophosphorus acid chemically bond with oxide or hydroxyl groups on the metal surface layer 52 or chemically bond with the hydroxyl or alkoxide group of the organometallic coating 54, resulting in a durable film. It is believed that the organophosphorus acid forms a self-assembled monolayer on the surface of the substrate (i.e., the metal surface layer 52 or organometallic coating 54). Self-assembled layers or films are formed by the chemisorption and spontaneous organization of the material on the surface of the substrate. The organophosphorus acids useful in the practice of the invention are amphiphilic molecules that have two functional groups. The first functional group, i.e., the head functional group, is the polar phosphorus acid group and attaches by physical attraction or by chemical bonding to the surface of the substrate. The second functional group, the organophosphorus acid group, i.e., the tail, extends outwardly from the surface of the substrate.

Typically, the hydrophobic coating layer 56 is adhered to the metal surface layer 52 on the exterior surfaces of the reservoir 10 and dispensing device 30, rendering the exterior surfaces of the components hydrophobic. After application of the hydrophobic coating layer 56 to the entire metal surface layer 52, select areas of the hydrophobic coating layer 56 may be removed from the metal surface layer 52 on the interior surfaces of the components to expose the metal surface layer 52, which is hydrophilic. The hydrophobic coating layer 56 may be removed from the interior surfaces of the components in whole or in part. This removal of the hydrophobic coating layer 56 allows for exposure of the hydrophilic metal surface layer 52 to the fluid, which is usually aqueous, being passed through the nebulizer 100. Select, precise removal of the hydrophobic coating layer 56 may be done, for example, by plasma etching or UV-ozone etching. Removal of the hydrophobic coating layer 56 from select areas to expose the hydrophilic metal surface layer 52 allows for the formation of surface energy "patterns" on the nebulizer component surfaces; for example, channels to direct fluid flow in specific directions, such as drawing fluid into the pores of the microchannels 32. Such energy patterns also provide a well-controlled capillary force over time, promoting a consistent flow rate.

Thus, the present invention also provides a method of altering the surface energy of one or more components of a mesh nebulizer 100, to form the mesh nebulizers described above and shown in FIGS. 2A, 2B, 3A, and 3B. The method comprises: a) depositing a metal surface layer 52 on surfaces of the component, wherein the metal surface layer 52 comprises any of those described above; b) forming a hydrophobic coating layer 56 comprising an organo-silicon or a self-assembled monolayer of an organophosphorus acid directly on the metal surface layer 52 or indirectly on the metal surface layer 52 through an intermediate organometallic coating 54; and c) removing select areas of the hydrophobic coating layer 56 to expose the metal surface layer 52. Typically, the hydrophobic coating layer 56 is selectively removed (such as via UV-ozone etching) from at least a portion of the metal surface layer 52 on the interior surfaces of the reservoir 10 and dispensing device 30. Deposition of the metal surface layer 52 and hydrophobic coating layer 56 may be accomplished as discussed above. Alternatively, the hydrophilic metal surface layer 52 may be exposed where desired by masking those desired areas prior to applying the hydrophobic coating layer 56 to the metal surface layer 52, and removing the mask after application of the hydrophobic coating layer 56. Either of these methods may be used to prepare the components of the nebulizer of the present invention as shown in FIGS. 3A and 3B, but removing select areas of the hydrophobic coating layer 56 to expose the metal surface layer 52 is preferred.

In certain examples of the present invention, the hydrophobic coating layer 56 has terminal functional groups that are capable of initiating polymer growth when exposed to a source of polymerizable monomer; and a hydrophilic polymeric coating layer 60 chemically bonded to and propagated from the terminal functional groups on the hydrophobic coating layer 56 on the interior surfaces of the reservoir 10 and dispensing device 30. In a particular example of the present invention, the hydrophobic coating layer 56 comprises a self-assembled monolayer of an organophosphorus acid, and the self-assembled monolayer of the organophosphorus acid has terminal functional groups; that is, the omega or terminal portion of the tail contains a functional group.

The functional groups on the hydrophobic coating layer 56 are capable of initiating polymer growth when exposed to a source of polymerizable monomer, and thus the hydrophobic coating layer 56 can serve as an anchor or primer for a subsequently applied coating 60 with co-reactive functional groups. As an example, the organophosphorus acid can contain terminal amino and/or carboxylic acid groups and the subsequently applied layer 60 can be an epoxy containing resin or polymer. The amino and/or carboxylic acid groups are reactive with the epoxy groups resulting in a multilayer coating with good adhesion between the organophosphorus layer and the subsequently applied layer obtained from the epoxy resin or polymer.

The polymeric coating layer 60 may alternatively be prepared by polymerizing one or more ethylenically unsaturated monomers via a living polymerization process such as ATRP, propagated from the terminal functional groups. Exemplary ethylenically unsaturated monomers include hydrophilic (meth)acrylates and (meth)acrylamides, including those with ammonium chloride groups, poly(ethylene glycols), phosphate salts, etc. [2-(Methacryloyloxy)ethyl] dimethyl-(3-sulfopropyl)ammonium hydroxide, 2-acrylamido-2-methyl propane sulfonic acid, and salts thereof are the two most commonly used monomers. The polymeric coating layer 60 is hydrophilic, and is designed to allow for consistent wetting by the fluid 40 as noted above, facilitating droplet formation through a maximum number of the microchannels 32.

Figure 4C:
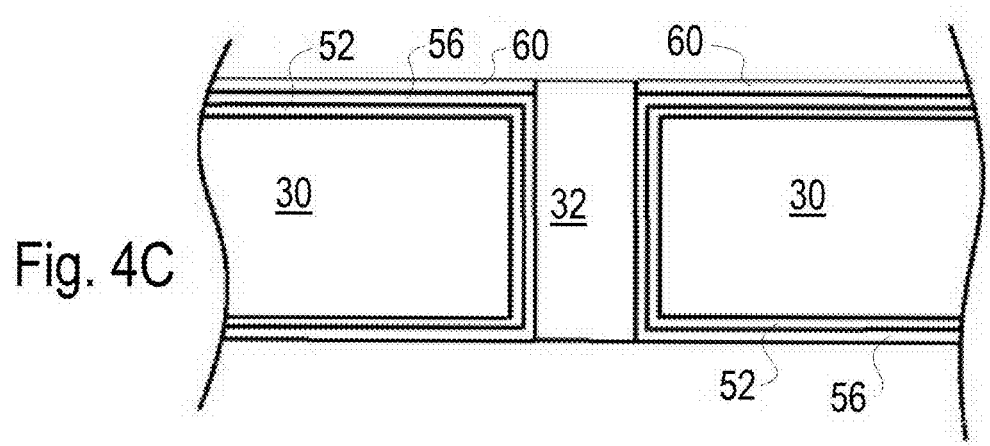
Figure 4D:
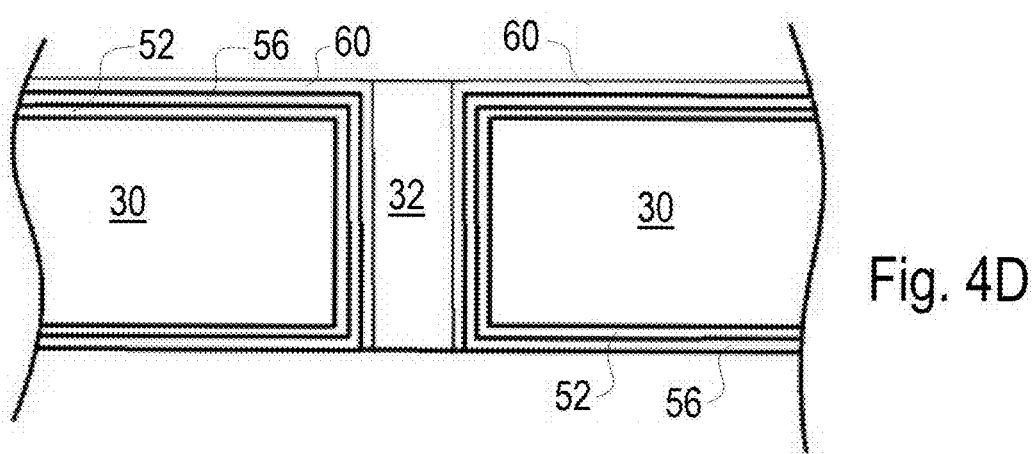

Typically, the polymeric coating layer 60 is propagated from the terminal functional groups on the hydrophobic coating layer 56 on the interior surfaces of the reservoir 10 and dispensing device 30, rendering the interior surfaces of the components hydrophilic. In order to promote propagation of the polymeric coating layer 60 only on the desired areas (i. e., interior surfaces), undesired areas may be masked prior to forming the polymeric coating layer 60 on the hydrophobic coating layer 56, and removing the mask after formation of the polymeric coating layer 60. As shown in FIG. 4C, the polymeric coating layer 60 may be on the interior surface of the component only, or as shown in FIG. 4D, the polymeric coating layer 60 may extend into the microchannel 32, coating the surface thereof. Alternatively, the polymeric coating layer 60 may be formed on the entire surface of the hydrophobic coating layer 56, and then subsequently removed from select areas such as the exterior surface of the component, using techniques known in the art, to expose the hydrophobic coating layer where desired.

The mesh nebulizers of the present invention utilize combinations of surface treatments to impart a wide variance of surface energy across the nebulizer component surfaces. Furthermore, the robustness of the surface treatments allows the component surfaces to retain that surface energy over time when the device is exposed to various fluids. These properties allow for consistent operation of the mesh nebulizer throughout its service life such as by minimizing build-up of organic materials due to adsorption onto the apparatus surfaces, which may, for example, obstruct the apertures of the dispensing device.

Whereas particular embodiments of this invention have been described above for purposes of illustration, it will be evident to those skilled in the art that numerous variations of the details of the present invention may be made without departing from the scope of the invention as defined in the appended claims.

What is claimed is:

1. A mesh nebulizer comprising a reservoir and a dispensing device that comprises a microarray of microchannels, wherein the reservoir and dispensing device are configured to allow a fluid to flow from the reservoir through the dispensing device and exit the dispensing device as an aerosol, and wherein the reservoir and dispensing device comprise:

1) an interior surface;

2) an exterior surface that opposes the interior surface;

3) a metal surface layer applied to the interior and exterior surfaces and comprising one or more of silver, gold, palladium, platinum, rhodium, iridium, tantalum, aluminum, copper, titanium, iron, chromium, alloys thereof, and oxides thereof; and 4) a hydrophobic coating layer comprising an organosilicon or a self-assembled monolayer of an organophosphorus acid, adhered to the metal surface layer on the interior and/or exterior surfaces of the reservoir and dispensing device, wherein the hydrophobic coating layer is adhered to the metal surface layer either directly or indirectly through an intermediate organometallic coating.

2. The mesh nebulizer of claim 1, wherein select areas of the hydrophobic coating layer are removed to expose the metal surface layer on the interior surfaces of the reservoir and dispensing device.

3. The mesh nebulizer of claim 1, wherein the hydrophobic coating layer 4) is chemically bonded directly to the metal surface layer 3).

4. The mesh nebulizer of claim 1, wherein the dispensing device comprises a mesh or perforated plate.

5. The mesh nebulizer of claim 1, wherein the hydrophobic coating layer 4) comprises a self-assembled monolayer of organophosphorus acid that is adhered to the metal surface layer 3) indirectly through the intermediate organometallic coating.

6. The mesh nebulizer of claim 5, wherein the intermediate organometallic coating comprises a polymeric metal oxide having unreacted alkoxide and/or hydroxyl groups.

7. The mesh nebulizer of claim 1, wherein the hydrophobic coating layer has terminal functional groups that are capable of initiating polymer growth when exposed to a source of polymerizable monomer; and wherein the mesh nebulizer further comprises:

5) a polymeric coating layer chemically bonded to and propagated from the terminal functional groups on the hydrophobic coating layer on the interior surfaces of the reservoir and dispensing device.

8. The mesh nebulizer of claim 7, wherein the polymeric coating layer 5) is prepared from a reaction mixture comprising one or more of [2-(Methacryloyloxy)ethyl]dimethyl-(3-sulfopropyl)ammonium hydroxide, 2-acrylamido-2-methyl propane sulfonic acid, and salts thereof, via ATRP.

* * * * *